United States Patent [19]

Byrne et al.

[11] Patent Number: 5,653,700
[45] Date of Patent: Aug. 5, 1997

[54] DEVICE FOR FEMALE TRANSIENT URINARY CATHETERISATION

[75] Inventors: Philip Owen Byrne, Newcastle-Upon-Tyne; Julian Richard Minns, Durham, both of England

[73] Assignee: British Technology Group Ltd., London, England

[21] Appl. No.: 553,660

[22] PCT Filed: May 17, 1994

[86] PCT No.: PCT/GB94/01052

§ 371 Date: Nov. 16, 1995

§ 102(e) Date: Nov. 16, 1995

[87] PCT Pub. No.: WO94/26342

PCT Pub. Date: Nov. 24, 1994

[30] Foreign Application Priority Data

May 18, 1993 [GB] United Kingdom ............... 9310169
Jul. 20, 1993 [GB] United Kingdom ............... 9315048
Oct. 20, 1993 [GB] United Kingdom ............... 9321584

[51] Int. Cl.⁶ ........................... A61F 5/44; A61B 5/00
[52] U.S. Cl. ...................... 604/329; 604/328; 128/761
[58] Field of Search ........................... 604/328, 329, 604/330, 331; 128/760, 761, 763, 765, 768

[56] References Cited

U.S. PATENT DOCUMENTS 3,894,540  7/1975  Bonner, Jr. ...................... 604/349
4,889,533  12/1989 Beecher .......................... 604/330
4,986,823  1/1991  Anderson et al. ................ 604/329
5,045,078  9/1991  Asta .
5,234,409  8/1993  Goldberg et al. ................. 604/329

FOREIGN PATENT DOCUMENTS 0541091   5/1993  European Pat. Off. .
2555903   6/1985  France .
2150836   7/1985  United Kingdom .
90/04428  5/1990  WIPO .

*Primary Examiner*—John G. Weiss
*Assistant Examiner*—David J. Cho
*Attorney, Agent, or Firm*—Cushman Darby & Cushman IP Group of Pillsbury Madison & Sutro, L.L.P

[57] ABSTRACT

A device to facilitate self-catheterisation in women suffering from deviation from normal bladder function is provided. The device includes a handle designed for manipulation by a patient and a catheter co-operable with the handle such that the catheter can be inserted into the patient's urethra by manipulation of the handle. The device has a flexion portion to allow the catheter to be positioned in a desired orientation relative to the handle for ease of insertion. The handle and catheter may be designed as a one-piece disposable construction or may be separate elements, the handle being useable with disposable catheters. The flexion portion may be an articulation structure, such as a ball-and-socket joint. Catheterisation is further facilitated by the provision of a mirror and/or light source on or associated with the handle.

14 Claims, 3 Drawing Sheets

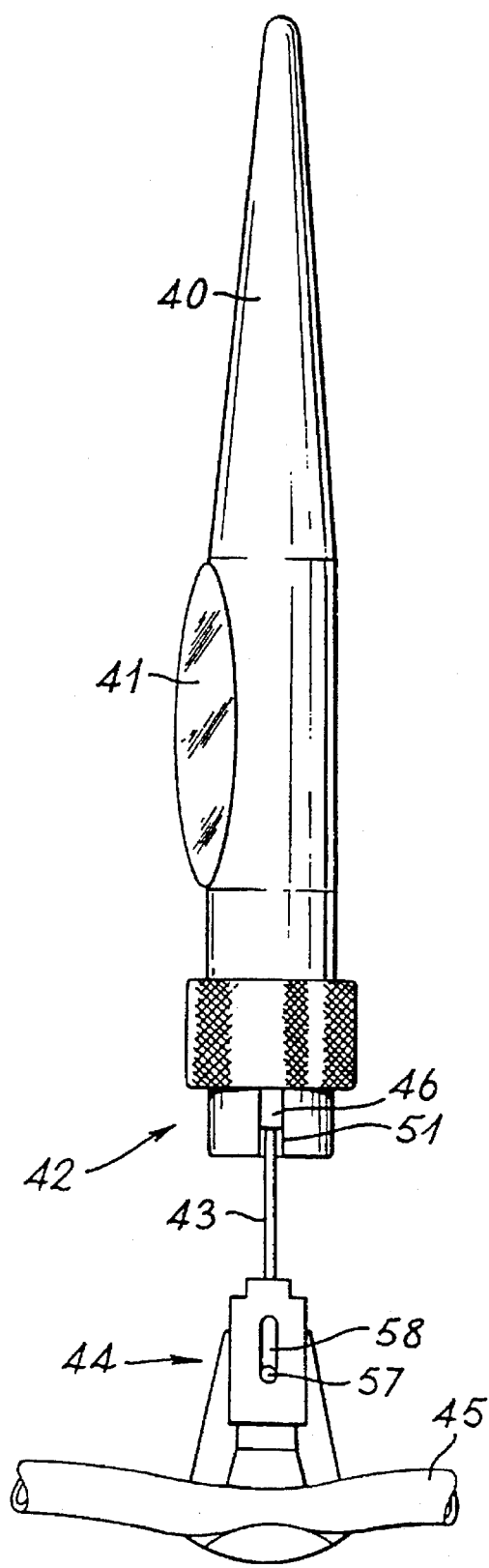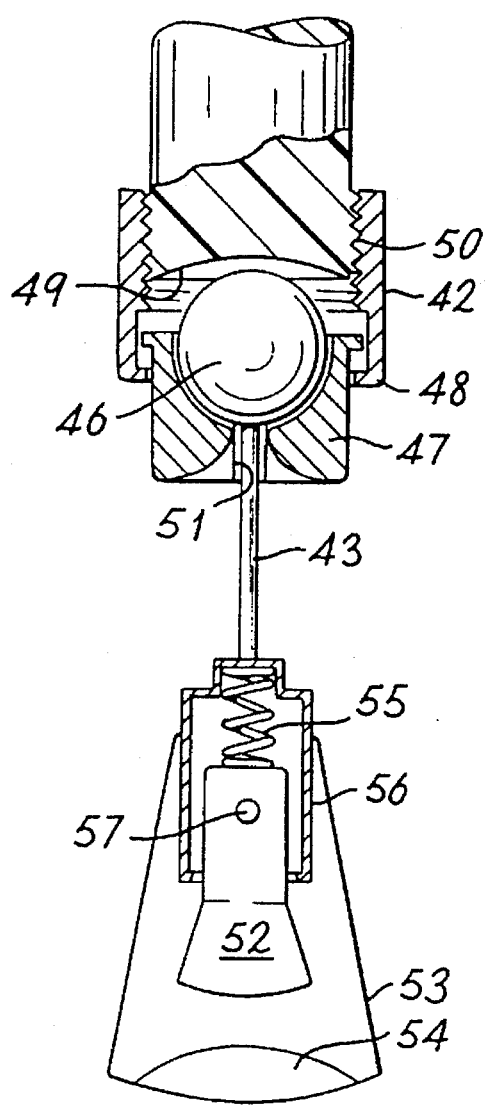
Fig. 7
Fig. 8

DEVICE FOR FEMALE TRANSIENT URINARY CATHETERISATION

This application claims benefit of international application PCT/GB94/01052, filed May 17, 1994.

BACKGROUND OF THE INVENTION

This invention relates to a device for female transient urinary catheterisation.

Deviation from normal bladder function in a patient can involve problems of urinary retention, whereby the bladder is unable to evacuate urine. This dysfunction can result from a number of different causes, such as congenital defects in the nerve connections to the brain, nerve injuries resulting from trauma to the spinal cord, extensive abdominal surgical operations, infection and various diseases. If the sphincter muscle is too tight or the bladder muscles are too lax the patient may be able to urinate but may be unable to completely empty the bladder during urination.

Patients with urinary retention require catheterisation to enable the bladder to be satisfactorily emptied. In some cases a urine collection bag and an indwelling urethral catheter are used, the catheter forming a passageway from the bladder to the externally-carried collection bag which can regularly be emptied. This arrangement, however, is cumbersome and moreover leaves the patient at increased risk of infection, bacteria being able to grow and track along the catheter from the collection bag or around the catheter along the urethra.

The alternative and more acceptable solution is the insertion of a transient urethral catheter to allow the patient to void in the bathroom when appropriate or on a predetermined time schedule, such as every three to four hours. For women, this intermittent self-catheterisation can be very difficult to carry out, since the patient must be able to locate the urinary meatus accurately in order to insert the catheter into the urethra. With presently available devices the patient accomplishes this with the aid of a separate mirror held at an appropriate angle, inserting the catheter along the urethra (about 3-4 cm) until its end reaches the bladder. The mirror must be held by the patient, the self-catheterisation thus becoming a two-handed operation, or the mirror must be supported in front of the patient in some way in a position whereby the patient has the required view. Additionally the catheter can be difficult to grip and manipulate, being only a thin, flexible plastic tube with a special slippery surface to aid insertion.

Patent Application FR 2 555 903 describes an intermittent catheterisation device comprising a handle and a catheter tube, the handle being used to facilitate the introduction of the catheter tube into the urethra. Once the catheter tube is engaged with the handle their relative positions are fixed except for the limited flexibility permitted by the slight degree of pliancy of the catheter.

SUMMARY OF THE INVENTION

It is an object of the present invention to obviate the drawbacks of known devices and to provide a medical device to increase the ease with which women can carry out intermittent urinary self-catheterisation.

According to the invention there is provided a device for female transient urinary catheterisation comprising a handle designed for manipulation by a patient and a catheter co-operable with the handle such that the catheter can be inserted into a patient's urethra by manipulation of the handle, the device being provided with a flexion portion to allow the catheter to be positioned in a desired orientation relative to the handle.

With this construction, the handle provides a means of facilitating the insertion of the catheter without need for the patient to grip the catheter itself to insert it into the urethra. The movement allowed by the flexion portion permits the patient to set the device into a position most appropriate for her particular anatomy and for the particular circumstances of use.

In one form of the invention the handle and the catheter are integrally connected in such a way that the two can be folded together by way of the flexion portion. With this construction, the handle and catheter unit can be stored as a flat pack, the catheter being folded out from the handle to form a transverse projection for use. This device can be manufactured as a disposable item.

In another form of the invention the handle and the catheter are separate elements and the flexion portion is at least partly incorporated in or associated with the handle. This allows the use of the device with conventional cheap disposable urinary catheters, the handle being reusable.

The flexion portion can be provided in any appropriate manner to allow flexion by distortion or by articulation. Preferably, the flexion portion comprises a tubular section of corrugated or other form bendable by deflection, which may be incorporated in the catheter or in a part of the handle. Alternatively, the flexion portion may comprise an articulation means, such as a ball and socket joint. This joint may be incorporated in the handle or the two parts of the joint may form part of the handle and the catheter respectively, for snap-fit interconnection in a watertight manner. To facilitate yet further use of the device, means may be provided for retaining the catheter in at least one selected orientation relative to the handle.

In the case of a separate and interconnectable handle and catheter, the handle of the device may be designed to store one or more catheters. With this construction, one or a number of disposable catheters may be contained within the handle prior to use and it is then easy for the patient to store and carry the whole assembly in a handbag, for example.

Preferably, in any form of the invention, a mirror is provided on the handle. This facilitates use of the device by allowing the patient to see the meatus of the urethra without needing to use a separate mirror. The mirror may be planar, convex or concave to provide a field of view as most appropriate. The mirror may be a filmed coating, its shape depending on the design of the part of the handle on which the coating is applied.

The handle may additionally or alternatively incorporate a light source arranged to provide illumination to facilitate catheter insertion.

It is clear that a number of features described above, such as a catheter storage handle construction, or a mirror and/or a light source on or associated with the handle, can be provided additionally or alternatively to other aspects of the invention, these features in themselves providing means to facilitate self-catheterisation.

In a further aspect of the invention, there is provided a handle for manipulation by a patient in the process of urinary catheterisation, for use in a device of the invention in any of the various forms.

BRIEF DESCRIPTION OF THE DRAWINGS

The invention will now be described by way of example with reference to the accompanying drawings, in which:

FIG. 7 illustrates a device according to the invention suitably adapted to employ conventional disposable urinary catheters; and FIG. 8 shows in cut-away form the functional details of a swivel joint and locking means of a catheter grip.

DETAILED DESCRIPTION OF THE INVENTION

Figure 1:
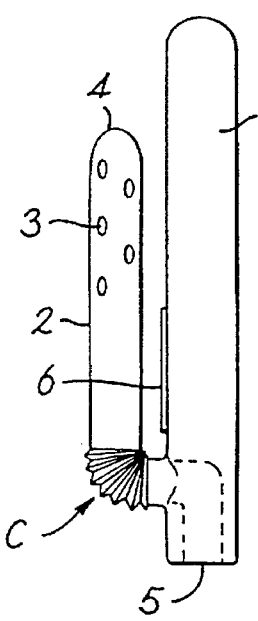
FIG. 1 shows a device according to the invention provided as an integral unit.

Referring to FIG. 1, an embodiment of the device of the invention shown in side view comprises an elongate handle 1 and an elongate hollow catheter 2. The handle is designed to be easy to grip and manipulate and for this purpose may have a specially shaped surface, whilst the catheter consists of a hollow tube with perforations 3 in the vicinity of catheter distal end 4 to allow urine to flow into the lumen of the catheter from the bladder. In this description, the distal end of the catheter is intended to signify the end of the catheter inserted during self catheterisation (Reference 4 in FIG. 1), in other words, that end of the catheter distal from the hand of the patient in manipulation of the device. Catheter 2 is fabricated integrally with handle 1, projecting laterally from, and adjacent to one end of, the handle. Alternatively the catheter and handle may be made as two separate elements and subsequently bonded by an appropriate technique, and this would be necessary if the two parts are designed in different materials. The lumen of the catheter continues into the handle and emerges at the end of the handle through an opening 5 which can also serve as a connection port for a urine collection bag. The catheter tube is relatively rigid but features a portion of circumferential corrugations C near the point at which the catheter meets the handle, these corrugations providing a flexible bending point allowing the catheter to be orientated as desired relative to the handle whilst maintaining the integrity of the lumen passage. For example, the catheter may be folded against the handle without any danger of the catheter tube collapsing. The corrugated form of flexion portion is preferred and such a design is known for application to, for example, flexible plastic drinking straws and fluid transfer pipelines, but other forms, bendable by distortion, are clearly equally applicable.

The handle 1 also carries a mirror 6 on the catheter side and located adjacent the point at which the catheter emerges. This mirror may have a planar surface, but is preferably concave to provide the patient with a magnified image. Alternatively the mirror surface may be convex to give the patient a wider field of view if this should be desirable. The mirror may, of course, be provided in any position on the handle which affords visualisation of the meatus, and may be off-centre with regard to the longitudinal axis of the handle.

Figure 2:
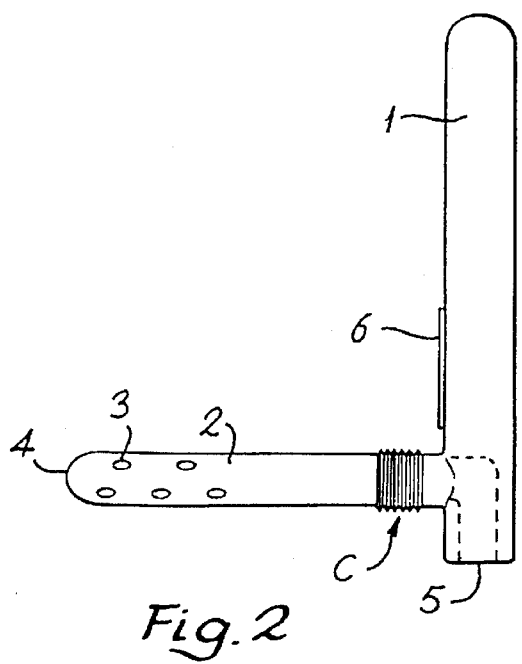
FIG. 2 shows the device of FIG. 1 in a use position.

When stored or carried the catheter 2 is folded flat against the handle 1 to take up a minimum space and the entire unit is sealed in a pre-sterilised package. A number of such packages can be carried in, say, the handbag of the patient. When the time comes for the patient to evacuate her bladder, she opens a package and folds out the catheter from the handle such that it projects transversely from the handle in a desired orientation, such as that shown in FIG. 2. She then holds the handle and, in a sitting position on a toilet seat, uses the mirror 6 to aid in locating the meatus of the urethra, inserting the distal end 4 of the catheter to the correct distance. The bladder will then drain via the perforations 3, the urine passing through the catheter lumen and out through the opening 5 into the toilet bowl. When evacuation is complete the catheter is removed from the urethra and the whole unit is either washed and retained for later re-sterilisation, or preferably discarded.

The handle/catheter unit is moulded from a suitable plastic material and the catheter part may be coated with PTFE or with a lubricant to facilitate insertion. This coating may be water-activated, the patient holding the catheter part under running water for a short period prior to use. Before use, the catheter may be protected by a clear plastic sheath to be removed directly before insertion. This allows the patient to unfold the catheter from the handle without touching it. The sterile packing may include lubricating jelly and/or it may contain an impregnated swab which the patient can use to cleanse the pubic area around the meatus immediately before catheter insertion.

Figure 3:
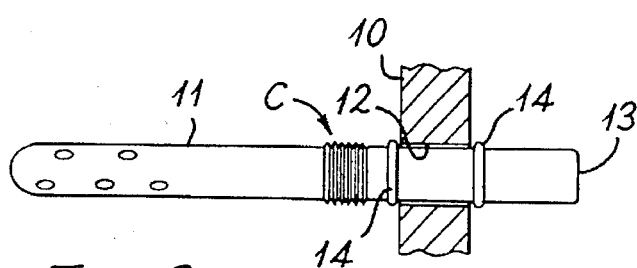
FIG. 3 is an elevational view, partly broken away and partly in cross-section, of an alternate device in accordance with the invention wherein the handle and catheter are provided as separate elements.

Another embodiment of the invention is illustrated in FIG. 3. In this case, the handle 10 and the catheter 11 are two separate elements, to be engaged for use. The handle 10 is of the same general form as already described, but features a catheter port 12 towards one end of the handle. The catheter 11 is of tubular form, perforated at its distal end as shown, the lumen terminating in an opening 13 at the proximal end of the catheter. Catheter 11 features a flexion portion C, again of crimped or corrugated form as shown, to enable the orientation of the catheter relative to the handle to be set at will to suit the requirements of the patient and thereby facilitate insertion. The catheter also features two circumferential ridges 14 axially spaced by a distance Just greater than the thickness of the handle, the material being sufficiently resilient for these ridges to be compressable to a small extent. These annular ridges 14 provide location means to ensure the catheter is inserted to the correct distance and also provide abutment means such that the catheter will not slide within the catheter port when the handle is being manipulated during the catheter insertion and withdrawal operations. Handle 10 is provided as a reusable element which need merely be washed after its use and stored until next required. Catheter 11 is a disposable item, stored in a pre-sterilised package. The patient therefore carries a single handle and a number of sterile packed catheters in, say, a handbag or pocket. When the time comes for urination, she opens the package without uncovering the distal end of the catheter and inserts the proximal end of the catheter into the port 12 in the handle, pushing the handle over one circumferential ridge 14 so that it locates and grips between the two ridges as shown in FIG. 3. This effectively locks the catheter in the handle during use and, after the outer wrapping has been completely removed, the patient inserts the catheter by means of the handle and with the aid of a mirror on the handle (not shown). After the bladder has been emptied and the catheter withdrawn from the urethra, the catheter can be pushed or pulled out of the catheter port and discarded, the handle being washed and retained for subsequent use with another sterile catheter.

Figure 4:
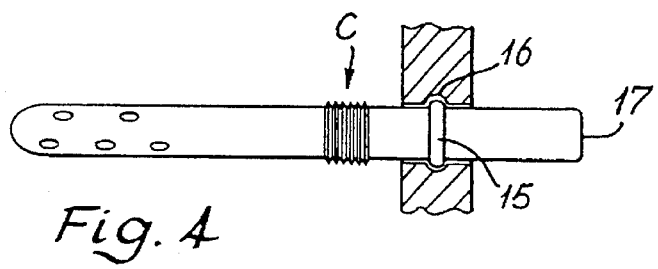
FIG. 4 is a view, partly in cross-section and partly broken away, of another alternative device according to the invention.

A similar device is shown in FIG. 4, the catheter in this case having a crimped or corrugated flexion portion C and having a single circumferential ridge 15 which locks into a peripheral annular groove 16 within the handle catheter port. Again, the material of the catheter is resilient enough for the catheter to be pushed into the handle such that the ridge 15 and groove 16 inter-engage, and similarly they can later be separated, but the engagement between the two is sufficient to firmly hold the catheter in position within the handle catheter port during insertion and withdrawal of the catheter from the urethra.

Figure 5:
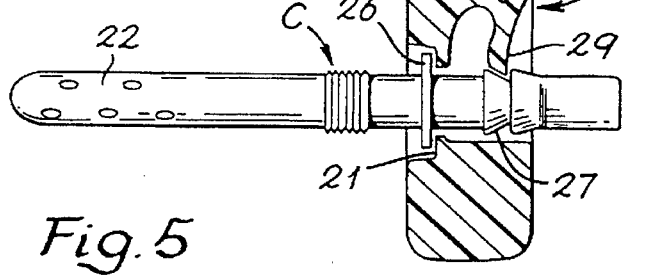
FIG. 5 is an elevational view, partly in cross-section, of a further alternate embodiment of the invention wherein the handle and catheter are provided as separate elements.

A further embodiment of the invention is shown in FIG. 5. Once again, the device consists of two parts; a handle 20 with a catheter port 21, and a separate catheter 22 with flexion portion C. The handle in this case features a hollow interior 23 extending from the end of the handle distant from the catheter port toward the region of the catheter port such that the major part of the handle is hollow, but the catheter port does not intercept this hollow interior 23. The end of the handle is formed as a removable or flip-type cap 24 and with this design one or a number of disposable catheters may be stored within the hollow interior of the handle until needed, when the cap 24 can be removed and a catheter (in its pre-sterilised package) taken out for use. Once again a mirror 25 is provided on the outside of the handle 20 in a position which allows easy visualisation of the urethral meatus. In this case, the mirror 25 is a reflective film coated onto the surface of the handle, the shape of the handle in this area determining the shape of the mirror, be it planar, convex or concave.

The catheter 22 has a circumferential ridge 26 and another group of circumferential saw-tooth ridges 27 as shown in FIG. 5, arranged to act as a one-way ratchet and to co-operate with a locking mechanism 28. The locking mechanism has a thumb- or finger-operated release lever 30 and a detent end 29, the locking mechanism being part of the moulding of the handle and being adapted for limited lever movement. In use, the catheter can be pushed into the handle until the ridge 26 and the ratchet ridges 27 abut against the corresponding parts of the catheter port. When the device has been used the release lever 30 can be operated to allow the catheter to be removed from the catheter port and discarded.

Figure 6:
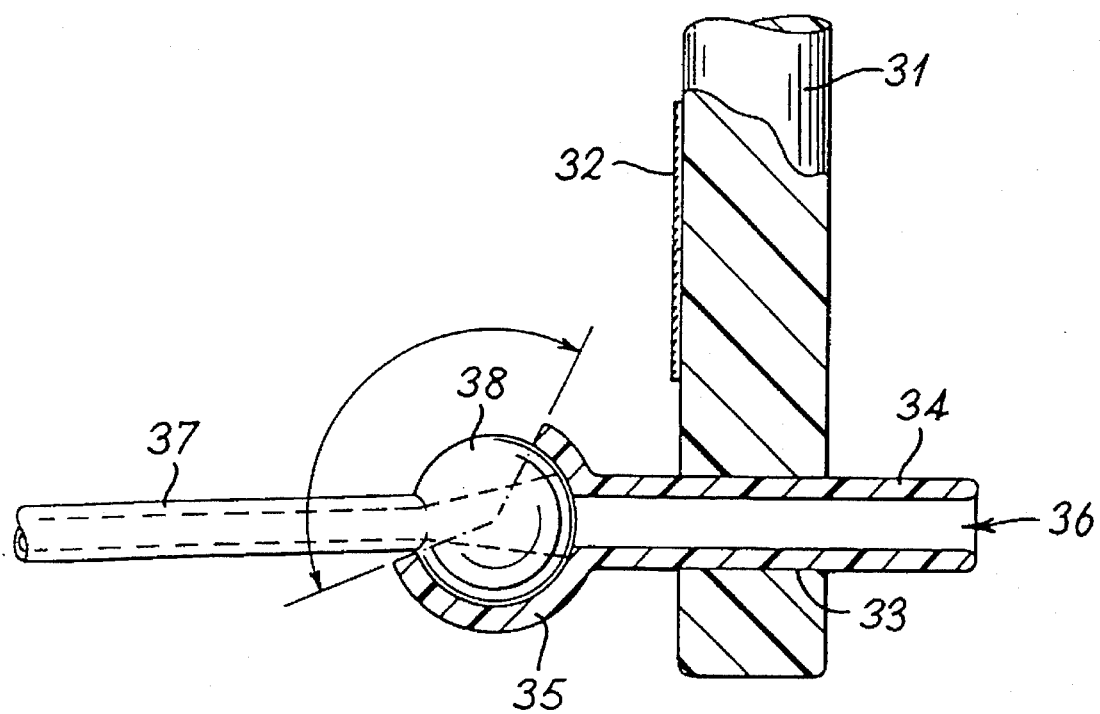
FIG. 6 is a view of another embodiment of the invention, partly broken away and partly in cross-section.

The further embodiment illustrated in FIG. 6 comprises a handle 31 with a mirror 32 and a catheter port 33. A tubular draining portion 34 is fixed within the catheter port, by adhesion or otherwise, and projects on both sides of the handle, terminating in a socket 35 on the mirror side of the handle and in an outlet opening 36 on the other side. Alternatively the handle 31 and draining portion 34 may be integrally formed.

The catheter 37 terminates in a ball 38 through which the lumen of the catheter passes, the ball being of complementary size and shape to the socket 35 such that the two can be snap-fitted together to form a watertight universal joint. As shown in the figure, the open part of the socket extends for less than 180° of the socket cross section to allow the snap-fit action; and the open part is angled so as to be offset from the axial orientation of the tubular portion 34. This is to allow the catheter to lie flat against the handle in a 'closed' position, whilst stored in its sterile package prior to use, and then folded out from the handle into a selected 'open' position when ready to use. The articulation provided by the ball and socket joint allows a wide range of movement appropriate to enable the patient to direct and locate the catheter into the urethra as required by means of the handle, whilst ensuring the integrity of fluid connection between the lumen of the catheter 37 and that of the tubular draining portion 34. The whole device may be supplied as a single disposable item, or the handle 31, with the tubular draining portion 34, may be reused with a new sterile catheter 37 which the patient herself can fit into the socket 35.

Whilst the above is described in the context of a 'ball and socket' arrangement, it is to be understood that the invention embraces other embodiments which allow rotational freedom between the catheter and the draining portion, for example a 'barrel and socket' connection allowing rotation in only one plane, preferably that passing through the longitudinal axis of the body of the handle. Furthermore, the device may feature means to positively retain the catheter in a preferred extended position after folding out from the handle.

In an alternative form, the above-mentioned device may be modified by incorporating the flexion portion of the device (be it an articulation means such as a ball and socket joint, a crimped section or otherwise) in, or associated with, the handle, and providing for attachment of a separate, standard catheter. The handle is designed as a reusable unit.

The advantage of this design is that the provision enabling orientation of the catheter to suit the requirements of individual patients is built into the handle, and need not be incorporated in the catheter itself. Conventional disposable urinary catheters can therefore be used in combination with the reusable handle, although some modification might be required to enable the catheters to positively couple to the handle connection.

In a preferred form the catheter can be locked, temporarily or permanently, in a set position so as to prevent movement during insertion. In this way, an individual patient may fix the handle/connection unit in an appropriate orientation to suit her own anatomy. Once set, the orientation is fixed and each disposable catheter subsequently fitted to the handle unit will therefore be correctly positioned for insertion. Alternatively, the rotatable connection may be folded and locked for packaging/storage such that the handle unit takes up as little room as possible. The rotatable connection may feature a suitable form of marking to enable a patient to re-orientate to a known position as required.

FIG. 7 illustrates a device according to the invention suitably adapted to employ conventional disposable urinary catheters and in which the device can be set to ensure that subsequently each catheter is held in a selected orientation.

The device comprises an elongate handle 40 with a mirror 41 arranged on one side of the handle body in an appropriate manner evident from consideration of the embodiments already described. At one end of the handle is a swivel joint and locking means 42 by means of which an arm 43 can be rotated and locked relative to the handle. The free end of the arm 43 carries a catheter grip 44 arranged to grip a standard catheter. Reference 45 in FIG. 7 denotes a section of the catheter tubing.

FIG. 8 shows in cut-away form the functional details of both the swivel joint and locking means 42 and of the catheter grip 44. The mechanism 42 provides a lockable universal joint serving as articulation means between the handle and the catheter, to give rotational freedom of movement in more than one plane. The joint by which the arm 43 and hence the catheter grip 44 can be rotated comprises a ball 46 from which the arm 43 extends, the ball held captive between the end 49 of the handle body and a collet 47, the collet being engaged and retained as shown by locking nut 48 which engages by threaded means 50 with the handle body. Tightening of the nut 48 will therefore serve to lock the ball 46, and thus the arm 43 and catheter grip 44, in a desired position. As can be seen in FIG. 7, the collet features a slot 51 allowing the arm 43 to be rotated into any position between 0° and 90° relative to the handle in the plane of the slot. Since the collet 47, when not locked in position, can rotate relative to the handle about the handle longitudinal axis, the patient can rotate the arm 43 so that it engages in the slot 51, and then by rotation of the arm about the longitudinal axis of the handle the collet can be rotated. This range of movement allows the patient to move the catheter grip 44 into any desired orientation relative to the handle 40 and to the mirror 41, and then lock the joint by means of locking nut 48 in a position which best suits her needs.

FIG. 8 also illustrates the components and operation of the catheter grip 44. This comprises a movable gripping element 52 and a spoon-shaped holder 53 with a bent lip 54, suitably sized such that the catheter tubing 45 can be held between the element 52 and the lip 54 as shown in FIG. 7. Movable gripping element 52 is spring biased in the direction of the lip 54 by means of a light spring 55 in housing 56, and is also provided with a small protruding spigot 57 which moves within an elongated slot 58 (FIG. 7) in the housing 56, parallel to the direction of the arm 43. A catheter can be gripped by retracting the gripping element 52 by means of manipulation of the spigot 57 against the force of the spring 55, inserting a catheter in the spoon-shaped holder 53 under the lip 54, and releasing the gripping element 52 such that it is moved under action of the spring against the catheter tubing. The limits of the slot 58 prevent the catheter being overly distorted by the gripping action, and the stiffness of spring 55 is selected so as to allow the use of a wide variety of catheter sizes with a common catheter grip whilst ensuring that the catheter is held firmly, irrespective of its size. The catheter-engaging surface of the bent lip 54 and/or the element 52 may be serrated or roughened to improve the grip on the catheter.

It is evident that operation of the device of FIGS. 7 and 8 allows orientation of the catheter relative to the handle as desired, whilst ensuring that, once the catheter grip 44 is set into a selected position by way of the swivel joint/locking means 42, each catheter subsequently inserted in the catheter grip 44 will be held in the optimum orientation.

In a preferable form of device, the handle may be provided with an integral light source. This might be arranged to provide direct illumination to aid in location of the urethral meatus, or might be arranged such that illumination is provided by reflection of the light from a mirror surface provided on the handle itself. In either case, this is likely to be a useful feature when the patient is using the device in low light surroundings.

The device of the present invention is conveniently made of plastics material which can be readily cleaned and subjected to appropriate sterilisation procedures. For example, in the case of an embodiment featuring a handle and a separate catheter element, such as that shown in FIG. 5, the handle may be manufactured from polycarbonate material and the catheter from polypropylene material. As an alternative, inexpensive material, the handle may be made from cardboard, if necessary coated with a water resistant plastics layer.

Turning to the dimension of the device, it is envisaged that the handle part of the device measures between 6 and 15 cm in length, preferably from 10 to 12 cm, whilst the catheter element extends from the handle by a distance of between 4 and 10 cm, preferably from 6 to 9 cm, and has a cylindrical shape of diameter between 2.5 and 6 mm. Clearly the actual dimensions selected will depend to a large extent on the patient herself, and it is contemplated that the device will be designed in a variety of standard sizes over a selected range, although the device may alternatively be made if necessary to suit particular requirements of a patient.

Whilst the invention has been described and illustrated in conjunction with specific embodiments thereof, it should be understood that these are in no way exhaustive of the invention which is intended to embrace all other embodiments falling within the spirit and scope of the appended claims.

We claim:

1. A device for female transient urinary catheterisation comprising:

a handle designed for manipulation by a patient, said handle having a longitudinal axis; and a catheter projecting from the handle and co-operable with the handle such that the catheter can be inserted into a patient's urethra by manipulation of the handle, the catheter forming an elongated fluid conduit having a longitudinal axis, an insertion end, and an opposite end spaced from the insertion end, said catheter having a passage for discharge of said fluid, one of the catheter and the handle being provided with a flexion portion whereby the catheter can be displaced relative to said handle so that an orientation of said longitudinal axis of said catheter relative to said longitudinal axis of said handle can be changed to a desired orientation for insertion into the urethra.

2. A device according to claim 1, wherein the handle and the catheter are integrally connected in such a way that the two can be folded together by way of the flexion portion.

3. A device according to claim 1 wherein the flexion portion is at least partly incorporated in or associated with the handle and a separate catheter element is connectable thereto.

4. A device according to any preceding claim, wherein the flexion portion comprises a tubular section of corrugated or other form bendable by distortion.

5. A device according to claim 3, wherein the flexion portion comprises an articulation means.

6. A device according to claim 5 wherein the handle and the catheter are respectively provided with corresponding complementary elements of a swivel joint, the two elements being engageable in snap-fit connection.

7. A device according to claim 5, wherein a catheter grip is provided for selectively holding or releasing a catheter connected to the handle by way of the articulation means.

8. A device according to any of claims 5 to 7, in which the articulation means is a universal ball joint.

9. A device according to claim 1 comprising means for retaining the catheter in at least one selected orientation relative to the handle.

10. A device according to claim 1, wherein the handle is constructed to store at least one catheter.

11. A device according to claim 1, wherein a mirror is provided on the handle to facilitate catheter insertion.

12. A device according to claim 11, wherein the mirror is a filmed coating on the handle.

13. A device according to claim 1, wherein the handle incorporates a light source arranged to provide illumination to facilitate catheter insertion.

14. A handle for manipulation by a patient in the process of urinary catheterisation, for use in a device according to claim 1.

* * * * *